United States Patent [19]
Allen

[11] Patent Number: 5,403,344
[45] Date of Patent: Apr. 4, 1995

[54] MULTI-FACETED SURGICAL NEEDLE

[75] Inventor: Richard C. Allen, New Bern, N.C.

[73] Assignee: American Cyanamid Co., Wayne, N.J.

[21] Appl. No.: 95,798

[22] Filed: Jul. 22, 1993

[51] Int. Cl.⁶ .............................................. A61B 17/04
[52] U.S. Cl. .................................................. 606/223
[58] Field of Search ................................ 606/222–227

[56] References Cited

U.S. PATENT DOCUMENTS

| | | | |
|---|---|---|---|
| 1,599,059 | 9/1926 | Morton | 606/223 |
| 2,092,929 | 9/1937 | Ovington | 606/222 |
| 4,237,892 | 12/1980 | Ritter et al. | 606/223 |
| 4,513,747 | 4/1985 | Smith | 606/223 |
| 4,932,961 | 6/1990 | Wong et al. | 606/223 |

Primary Examiner—Stephen C. Pellegrino
Assistant Examiner—Gary Jackson
Attorney, Agent, or Firm—C. F. Costello, Jr.

[57] ABSTRACT

A surgical suturing needle has a tapered needle head with a multi-faceted cross-section. The cross-section is formed by three circumferentially-spaced cutting edges formed at a primary angle and a plurality of extended legs, each extending from one of the primary angles and formed at a secondary angle. In addition, a plurality of connecting surfaces adjoin adjacent extended legs.

18 Claims, 3 Drawing Sheets

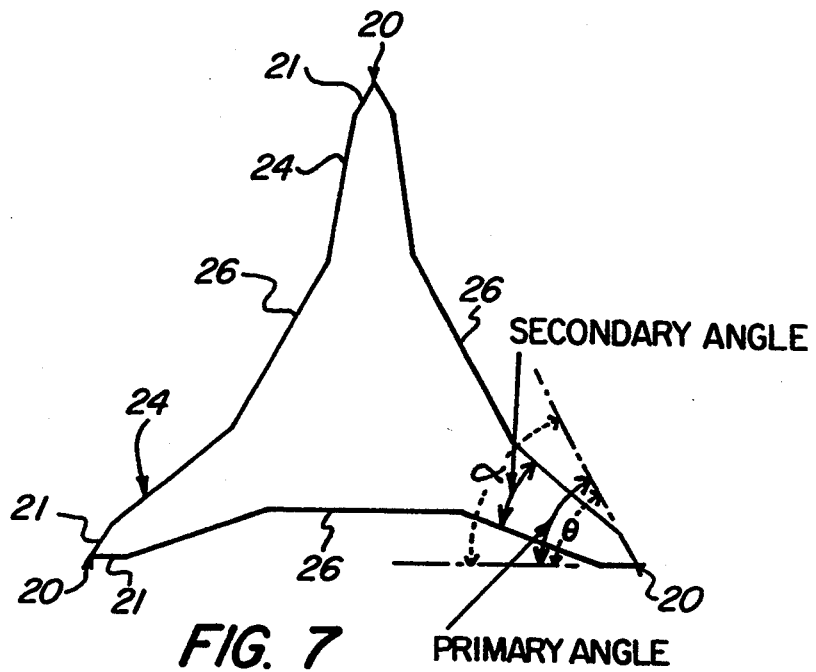
FIG. 7
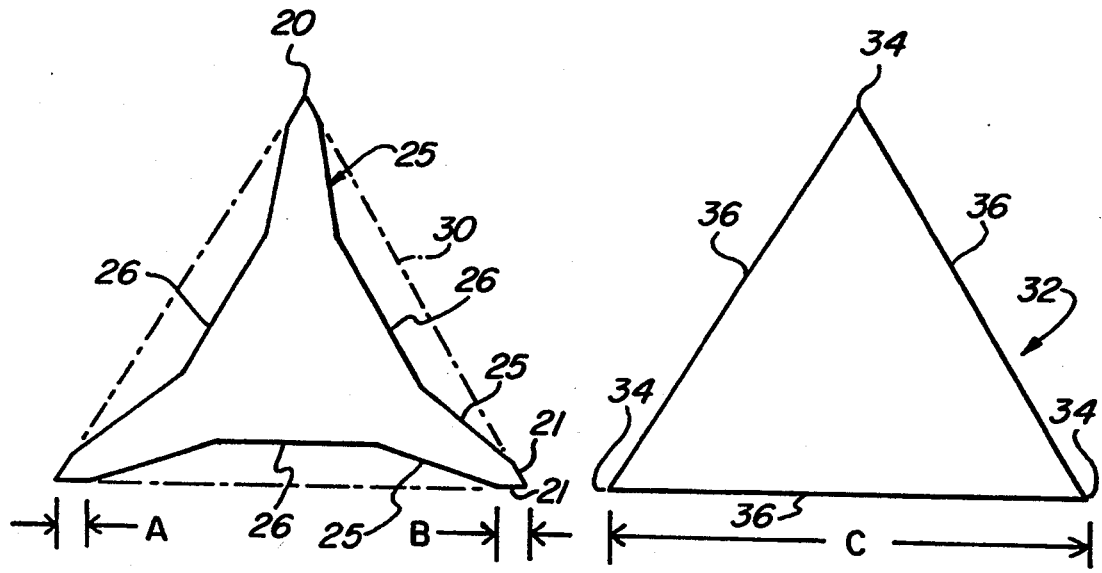
FIG. 8A
FIG. 8B

MULTI-FACETED SURGICAL NEEDLE

BACKGROUND OF THE INVENTION

1. Field of the Invention

The present invention relates to a surgical suturing needle for penetrating cutaneous and sub-cutaneous tissue. More particularly, the surgical needle is provided with a tapered needle head having a multi-faceted cross-section and a plurality of cutting edges, and is used generally for adjoining or closing adjacent portions of skin or tissue.

2. Description of the Prior Art

Suturing needles for applying sutures, or stitches, by hand in cutaneous and sub-cutaneous tissue are well known in the art. Typically, the sutures are used to close wounds or adjoin adjacent tissue, often at the conclusion of a surgical procedure. Suturing needles are usually made from a cut blank of material such as stainless steel. The cut blank is metal-worked using well known machining techniques to form the surgical suturing needle. The needle generally includes a shaft, a rear end portion with means to grip or secure a suturing thread and a needle head at a front end portion for puncturing skin and tissue through which the needle travels. The needle head typically includes a sharpened needle tip at its distal end and cutting edges.

An important consideration in designing surgical suturing needles is needle sharpness. Sharper needles require less force to penetrate the tissue and thus cause less tissue trauma. In addition, sharper needles reduce fatigue on the needle itself, making it less likely to bend or break during suturing. Needle sharpness is typically defined in terms of a so-called penetration force—the force necessary for a needle to puncture, or penetrate, the tissue. The penetration force is primarily determined by the design and sharpness of the needle point and the cutting edges formed on the needle head.

One example of a conventional surgical needle designed for improved needle sharpness is shown in U.S. Pat. No. 4,932,961, to Wong, et al. That patent discloses a needle having a tapered cutting edge with a five-sided cross-section. The needle has three fluted edges for cutting the tissue. The cross-section is basically triangular in shape, but indentations are provided in two fluted edges of the triangle to form the five sides and accentuate the third fluted edge.

However, further improvements in surgical needle design are desirable. The subject invention provides significant advances over conventional suturing needles by improving needle attributes such as needle sharpness, while also reducing the machining costs of manufacturing the needle.

SUMMARY OF THE INVENTION

Accordingly, it is a general object of the present invention to provide an improved surgical suturing needle.

It is another object of the present invention to provide a surgical suturing needle with superior ability to easily penetrate the skin and tissue.

It is a further object of the present invention to provide a surgical suturing needle that lessens tissue distortion.

It is still a further object of the present invention to provide a surgical suturing needle that minimizes the amount of material to be removed when sharpening the needle head, thus reducing machining costs.

In one aspect of the invention, the surgical suturing needle has a tapered needle head with a multi-sided cross-section. The cross-section comprises a plurality of circumferentially-spaced cutting edges, with each cutting edge formed at a primary angle, and a plurality of extended legs, with each leg extending from one of the cutting edges and formed at a secondary angle. A plurality of connecting surfaces adjoin adjacent extended legs.

In a preferred embodiment, the primary angles of the cutting edges are formed at a different angle than the secondary angle of the extended legs, and even more preferably the primary angles are larger than the secondary angles.

In another aspect of the invention, the surgical suturing needle provides a tapered needle head with a 15-sided cross-section. The cross-section comprises three circumferentially-spaced cutting edges, with each cutting edge having a base portion and two cutting surfaces formed at a primary angle, and an extended leg extending from the base of each cutting edge at a secondary angle. Three connecting surfaces adjoin adjacent extended legs.

In yet another aspect of the invention, the surgical needle comprises a needle shaft, suturing thread securing means at a rear end of the needle shaft, and a tapered needle head at a front end of the needle shaft. The needle head tapers to a needle point and has a 15-sided cross-section comprised of three circumferentially-spaced cutting edges, with each cutting edge having a base portion and two cutting surfaces formed at a primary angle, an extended leg extending from the base of each cutting edge at a secondary angle, and three connecting surfaces, with each surface adjoining adjacent extended legs.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 7 is a cross-sectional view of the needle head of the present invention illustrating primary and secondary angles of the needle head;

FIG. 8A is a cross-sectional view of the needle head in accordance with the present invention;

FIG. 8B is a cross-sectional view of a conventional needle head; and

DESCRIPTION OF THE PREFERRED EMBODIMENTS

Figure 1:
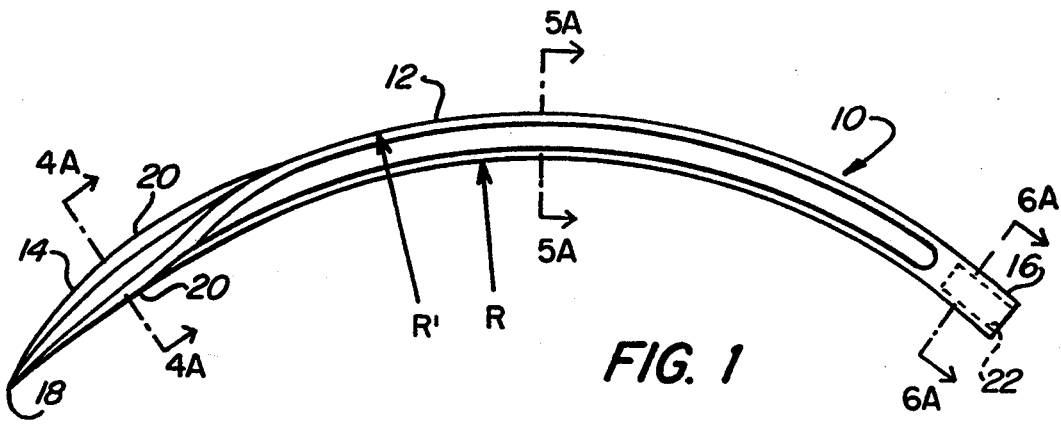
FIG. 1 is a side elevational view of a surgical suturing needle of the present invention.
Figure 2:
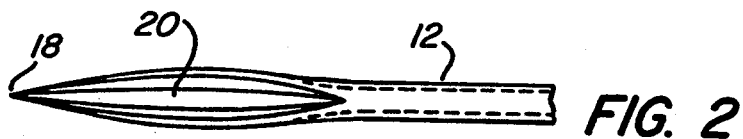
FIG. 2 is a partial bottom plan view of the distal end of the surgical suturing needle of the present invention.
Figure 3:
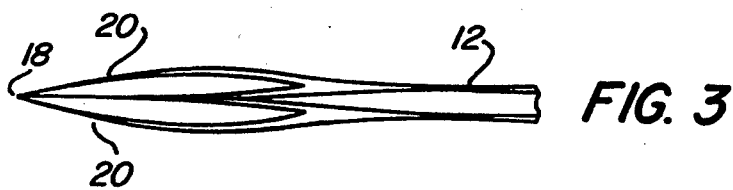
FIG. 3 is a partial top plan view of the distal end of the surgical suturing needle of the present invention.

The general shape of the surgical suturing needle 10 in accordance with the subject invention is shown in FIG. 1. A needle body 12 is preferably arcuate in shape along radius R and tapers at its distal end along radius R' at one side to form a tapered needle head 14. The needle head is shaped to have a needle point 18 and a plurality of cutting edges 20 that are shown in FIGS. 1 through 3 and will be discussed in detail below.

Figures 4, 5, 6:
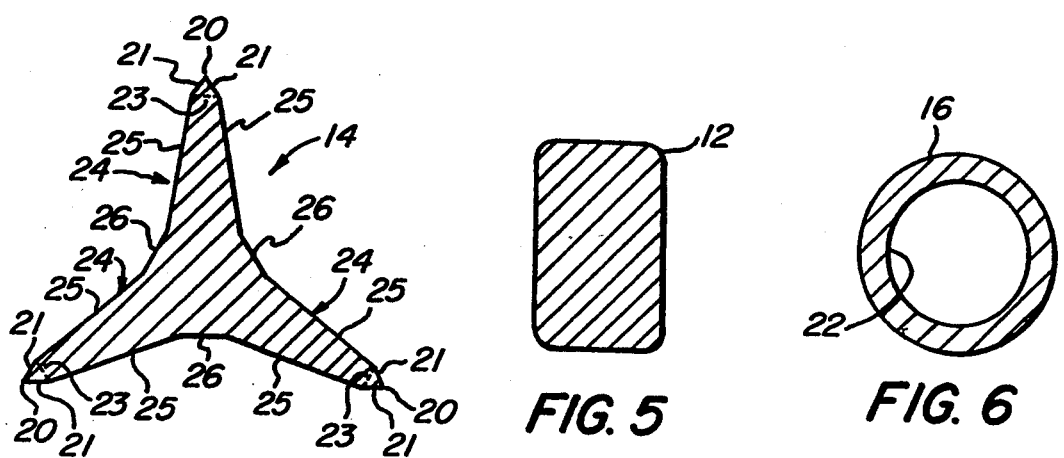
FIG. 4 is a cross-sectional view along plane 4A—4A in FIG. 1 of a needle head of the surgical suturing needle of the present invention.
FIG. 5 is a cross-sectional view along plane 5A—5A in FIG. 1 of a needle shaft of the surgical suturing needle of the present invention.
FIG. 6 is a cross-sectional view along plane 6A—6A in FIG. 1 of a proximal end of the surgical suturing needle of the present invention.

The suturing needle can be made from a conventional cut blank of material such as stainless steel in the shape of, for example, a wire. The cut blank is metal-worked to form the needle body 12 with a preferably rectangular cross-section as shown in FIG. 5. A rear end 16, or proximal end, of the needle is barrel-shaped with a circular cross-section as shown in FIG. 6, and includes an axial hole 22 for receiving and securing a suturing thread. Of course, other means besides the barrel-shaped rear end can be used for securing the suturing thread to the needle shaft. For example, a crimping channel, can be provided in the rear end of the needle 10.

In accordance with the subject invention, the distal end, or front end, of the needle is metal-worked to form a needle head 14 with a multi-faceted cross-section as shown in FIG. 4. The needle head features three circumferentially-spaced cutting edges 20, with each cutting edge defined by two cutting surfaces 21 and having a base portion 23. Each cutting edge is contiguous with an extended leg 24 at its base portion. FIG. 4 shows three extended legs 24, with each leg having a pair of tapered surfaces 25. Connecting surfaces 26 are spaced between two tapered surfaces to adjoin adjacent extended legs. FIG. 4 thus shows 15 different surfaces, or facets, that combine to form the needle head of the subject invention.

As shown in FIG. 7, the cutting edges 20 are formed at a primary angle $\theta$ that is preferably between 30° to 120°, and even more preferably around 60°. The tapered surfaces 25 of the extended legs 24 form secondary angles $\alpha$ preferably between 0° to 90°. The connecting surfaces 26 can be planar as shown in FIG. 4, or alternatively one or more connecting surfaces can be concave in shape to blend with the surfaces of the adjacent extended legs as shown, for example, in FIG. 9.

One advantage of providing the needle head with a cross-section in accordance with the subject invention is that a relatively small area of the needle is actually in contact with the tissue while it is being cut as compared to conventional needle heads. The needle head 14 is shaped so the only portion that substantially contacts the tissue during cutting is the three cutting edges 20. The extended legs 24 and connecting surfaces 26 are shaped to be inside an imaginary triangle (see dotted line 30 in FIG. 8A) bounded by the three cutting edges 20. This arrangement provides improved penetration performance, less tissue trauma and distortion and a reduced wound opening area.

Another advantage of the needle head design in accordance with the subject invention is the significant reduction in stock removal necessary to sharpen the cutting edges 20, which results in less machining time and reduced manufacturing costs. This advantage is made possible by the difference in angles between the cutting edges 20 and the extended legs 24 leading to the cutting edges. As shown in FIG. 7, for example, the primary angle $\theta$ formed by the cutting edge 20 is approximately 60°, while the secondary angle $\alpha$ is formed at approximately 30°. In this way, the extended legs, and for that matter the adjoining surfaces 26, only incidently contact the tissue as the needle passes through the skin and do not press against the tissue and skin while it is being cut. When forming the needle head, therefore, only cutting surfaces 21 of the cutting edges 20 must be machined and polished to the high degree necessary to cut the tissue.

This advantage is exemplified in FIGS. 8A and 8B. FIG. 8B illustrates a cross-section 32 of a conventional needle head that is substantially triangular in shape. In order to sharpen the cutting edges 34, the entire planar surface 36 between adjacent cutting edges must be machined. Therefore, the entire peripheral surface of the needle head will have to undergo stock removal in order to properly sharpen the cutting edges 34. In contrast, the needle head of the subject invention shown in FIG. 8A can be sharpened by removing stock from the relatively small surface area of cutting surfaces 21 that form the cutting edges 20.

The cross-sectional surface areas of the needle heads shown in FIGS. 8A and 8B are substantially equal because a smaller overall triangle is used in FIG. 8B. If distance C=3.35 [units] in FIG. 8B and distances A and B in FIG. 8A each equal 0.20 [units], then equation 1 shows the surface of any one side of the needle head to be sharpened in accordance with the subject invention. Equation 2 shows the difference between the surface of any one side of the needle head to be sharpened in the conventional needle head of FIG. 8B and the needle head of the subject invention shown in FIG. 8A.

$$A = 0.20 \atop \underline{B = 0.20} \atop A + B = 0.40 \qquad (1)$$

$$\begin{aligned} C &= 3.35 \\ C - (A + B) &= \begin{array}{r} 3.35 \\ -0.40 \\ \hline 2.95 \end{array} \end{aligned} \qquad (2)$$

$$\frac{2.95}{3.35} = 0.88 \qquad (3)$$

Thus equation 3 above illustrates an 88% reduction in stock removal to sharpen the needle head in FIG. 8A as opposed to sharpening the needle head in FIG. 8B. This significant reduction means less machining is necessary and thus less cost is involved in sharpening the needle. In accordance with the subject invention, anywhere from a 60% to 90% reduction in stock removal can be provided over a conventional triangular-shaped needle head.

Figure 9:
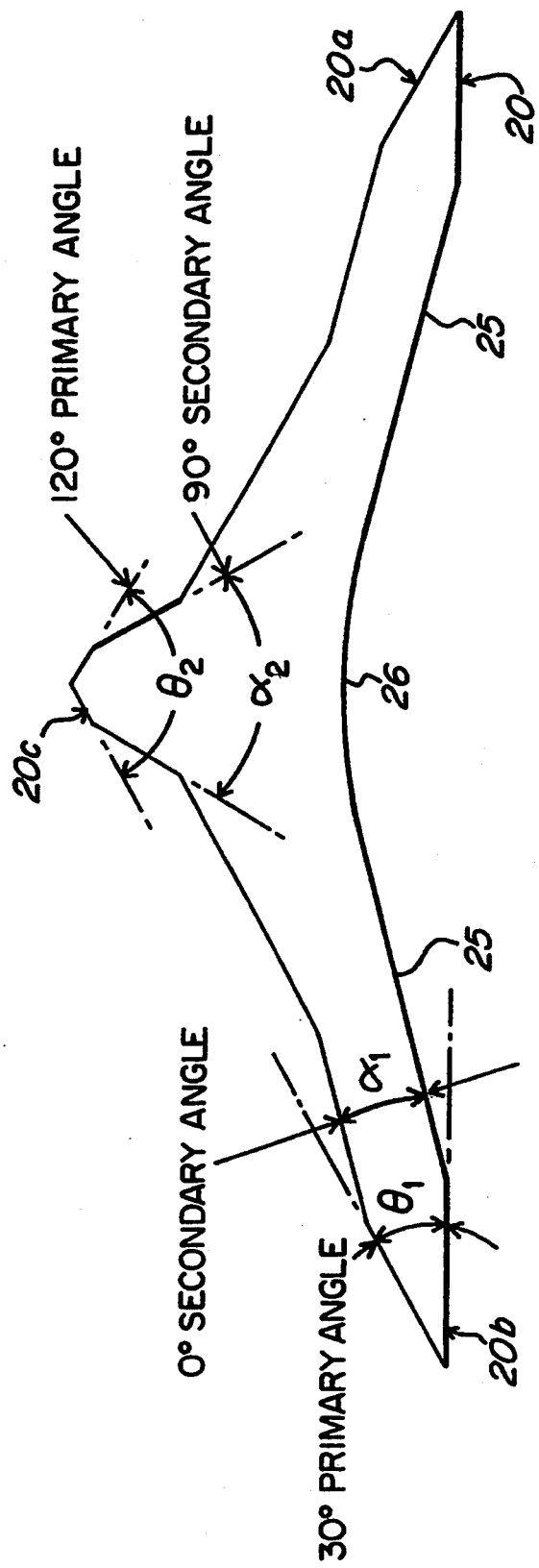
FIG. 9 is a cross-sectional view of a needle head in an alternative embodiment of the present invention.

As will be appreciated, the cutting edges 20 shown in FIG. 8A form the outline of a substantially equilateral triangle (see dotted line 30), and thus are formed at substantially the same primary angle $\theta$ of approximately 60°. However, the cross-section of the needle head need not form an equilateral triangle, and the cutting edges do not have to be formed at the same primary angle. For example, FIG. 9 shows cutting edges 20a and 20b formed at primary angle $\theta_1$, and cutting edge 20c formed at primary angle $\theta_2$. As FIG. 9 also illustrates, the secondary angles $\alpha$ can also vary from one another.

Although specific embodiments of the present invention have been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A surgical needle having a tapered needle head with a multi-sided cross-section, said cross-section comprising:
    a plurality of circumferentially-spaced cutting edges, each cutting edge having two cutting surfaces formed at a primary angle;
    a plurality of extended legs, with each leg extending from one of said cutting edges and contiguous with said respective cutting surfaces at a secondary angle smaller than the primary angle; and
    a plurality of connecting surfaces each adjoining adjacent extended legs.

2. A surgical needle according to claim 1, wherein said connecting surfaces are planar.

3. A surgical needle according to claim 1, wherein said connecting surfaces are concave.

4. A surgical needle according to claim 1, wherein the primary angles of each said cutting edge are formed at the same angle.

5. A surgical needle having a tapered needle head with a 15-sided cross-section, said cross-section comprising:
    three circumferentially-spaced cutting edges, each cutting edge having a base portion and two cutting surfaces formed at a primary angle;
    a plurality of extended legs, each leg extending from said base portion of one of said cutting edges and contiguous with said respective cutting surfaces at a secondary angle different from the primary angle; and
    three connecting surfaces, each connecting surface adjoining adjacent extended legs.

6. A surgical needle according to claim 5, wherein the primary angle of said cutting edges is larger than the secondary angle of said extended legs.

7. A surgical needle according to claim 5, wherein said primary angle of said cutting edges is a different angle than the secondary angle of said extended legs.

8. A surgical needle according to claim 5, wherein said connecting surfaces are planar.

9. A surgical needle according to claim 5, wherein said connecting surfaces are concave.

10. A surgical needle according to claim 5, wherein the primary angles of each said cutting edge are formed at the same angle.

11. A surgical needle, comprising:
    a needle shaft;
    suturing thread securing means at a rear end of said needle shaft;
    a tapered needle head at a front end of said needle shaft, said needle head tapering to a needle point and having a 15-sided cross-section, comprised of:
    three circumferentially-spaced cutting edges, each cutting edge having a base portion and two cutting surfaces formed at a primary angle;
    three extended legs, each leg extending from said base portion of one of said cutting edges and contiguous with said respective cutting surfaces at a secondary angle different from the primary angle; and
    three connecting surfaces, each connecting surface adjoining adjacent extended legs.

12. A surgical needle according to claim 11, wherein the primary angle of said cutting edges is larger than the secondary angle of said extended legs.

13. A surgical needle according to claim 11, wherein the primary angle of said cutting edges is a different angle than the secondary angle of said extended legs.

14. A surgical needle according to claim 11, wherein said connecting surfaces are planar.

15. A surgical needle according to claim 11, wherein said connecting surfaces are concave.

16. A surgical needle according to claim 11, wherein the primary angles of each said cutting edge are formed at the same angle.

17. A surgical needle according to claim 11, wherein a middle portion of said needle shaft is rectangular in cross-section.

18. A surgical needle according to claim 11, wherein said suturing thread securing means includes a barrel-shaped end with an axial hole for securing the suturing thread.

* * * * *